(12) United States Patent
Maxwell

(10) Patent No.: US 8,819,943 B2
(45) Date of Patent: Sep. 2, 2014

(54) SAFETY SCALPEL

(75) Inventor: Timothy J. Maxwell, Carp (CA)

(73) Assignee: Canica Design Inc., Almonte, Ontario (CA)

( * ) Notice: Subject to any disclaimer, the term of this patent is extended or adjusted under 35 U.S.C. 154(b) by 0 days.

(21) Appl. No.: 13/540,326

(22) Filed: Jul. 2, 2012

(65) Prior Publication Data
US 2012/0271333 A1    Oct. 25, 2012

Related U.S. Application Data

(63) Continuation of application No. 11/577,768, filed as application No. PCT/IB2005/003151 on Oct. 21, 2005, now abandoned.

(60) Provisional application No. 60/621,146, filed on Oct. 22, 2004.

(51) Int. Cl.
B26B 1/08      (2006.01)
A61B 17/32    (2006.01)

(52) U.S. Cl.
USPC ............................... 30/162; 30/335; 606/167

(58) Field of Classification Search
USPC ............ 30/162, 335, 336, 339; 606/166, 167, 606/170
See application file for complete search history.

(56) References Cited

U.S. PATENT DOCUMENTS

| | | | |
|---|---|---|---|
| 1,624,640 A | 4/1927 | Tietz | |
| 1,940,855 A | 12/1933 | Hugo | |
| 3,187,431 A | 6/1965 | Irmgard | |
| 3,262,205 A | 7/1966 | Arden | |
| 3,609,864 A | 10/1971 | Bassett | |
| 3,706,106 A | 12/1972 | Leopoldi | |
| 3,798,688 A | 3/1974 | Wasson | |
| 3,877,147 A | 4/1975 | Cummings | |
| D258,310 S | 2/1981 | LaHaye | |
| D263,445 S | 3/1982 | Gordin et al. | |
| 4,389,778 A | 6/1983 | Hakansson | |
| 4,522,206 A | 6/1985 | Whipple et al. | |
| 4,646,440 A | 3/1987 | Decker | |
| 4,649,919 A | 3/1987 | Thimsen et al. | |
| 4,660,287 A | 4/1987 | Decker | |
| 4,922,614 A | 5/1990 | Machida | |
| 4,941,232 A | 7/1990 | Decker et al. | |

(Continued)

FOREIGN PATENT DOCUMENTS

| | | |
|---|---|---|
| CA | 2128120 | 1/1996 |
| CA | 2265001 | 9/1999 |

(Continued)

OTHER PUBLICATIONS

European Patent Application No. 05797423.0, Extended European Search Report, mailed Nov. 4, 2010.

(Continued)

*Primary Examiner* — Hwei C Payer
(74) *Attorney, Agent, or Firm* — John S. Pratt; Kilpatrick Townsend & Stockton LLP

(57) ABSTRACT

A scalpel enabling both safe blade engagement or disengagement and safe passing among personnel during surgical procedures. The blade arm assembly of the scalpel is positionable in three positions, including a retracted position, an operational extended position and a fully extended position for engagement and disengagement of the blade.

5 Claims, 7 Drawing Sheets

(56) References Cited

U.S. PATENT DOCUMENTS

| | | |
|---|---|---|
| 4,960,419 A | 10/1990 | Rosenberg |
| 5,207,696 A | 5/1993 | Matwijcow |
| 5,250,063 A | 10/1993 | Abidin et al. |
| 5,275,606 A | 1/1994 | Abidin et al. |
| D345,290 S | 3/1994 | Sauber et al. |
| 5,312,429 A | 5/1994 | Noack |
| 5,314,417 A | 5/1994 | Stephens et al. |
| 5,411,512 A | 5/1995 | Abidin et al. |
| 5,423,843 A | 6/1995 | Werner |
| 5,431,672 A | 7/1995 | Cote et al. |
| 5,496,340 A | 3/1996 | Abidin et al. |
| 5,531,754 A | 7/1996 | Shackelford et al. |
| 5,571,127 A | 11/1996 | DeCampli |
| 5,599,351 A | 2/1997 | Haber et al. |
| 5,662,669 A | 9/1997 | Abidin et al. |
| 5,695,511 A | 12/1997 | Cano et al. |
| 5,702,397 A | 12/1997 | Goble et al. |
| 5,752,968 A | 5/1998 | Jolly et al. |
| 5,779,724 A | 7/1998 | Werner |
| 5,792,162 A | 8/1998 | Jolly et al. |
| 5,867,912 A | 2/1999 | Hickok et al. |
| 5,908,432 A | 6/1999 | Pan |
| 5,924,206 A | 7/1999 | Cote et al. |
| 5,938,675 A | 8/1999 | Gharibian |
| 5,938,676 A | 8/1999 | Cohen et al. |
| 5,957,945 A | 9/1999 | Bays |
| 5,984,918 A | 11/1999 | Garito et al. |
| 6,022,364 A | 2/2000 | Flumene et al. |
| 6,228,097 B1 | 5/2001 | Levinson et al. |
| 6,254,621 B1 | 7/2001 | Shackelford et al. |
| 6,402,770 B1 | 6/2002 | Jessen |
| 6,626,925 B2 | 9/2003 | Newman et al. |
| 6,629,985 B1 | 10/2003 | Kiehne |
| 6,757,977 B2 | 7/2004 | Dambal et al. |
| 6,949,109 B2 | 9/2005 | Iske et al. |
| 7,022,128 B2 * | 4/2006 | Morawski et al. ............ 606/167 |
| 7,101,382 B2 | 9/2006 | George |
| 7,748,124 B1 * | 7/2010 | Bell et al. ........................ 30/327 |
| 2002/0143352 A1 | 10/2002 | Newman |
| 2004/0098001 A1 | 5/2004 | Holman |
| 2004/0181247 A1 | 9/2004 | Kehr et al. |
| 2005/0065541 A1 | 3/2005 | Abidin et al. |
| 2009/0204137 A1 | 8/2009 | Maxwell |
| 2010/0268258 A1 | 10/2010 | Maxwell |

FOREIGN PATENT DOCUMENTS

| | | |
|---|---|---|
| CA | 2249996 | 10/2007 |
| CH | 84163 | 2/1990 |
| DE | 1144437 | 2/1963 |
| DE | 2648423 | 4/1978 |
| DE | 29703402 U | 4/1997 |
| EP | 0958788 | 11/1999 |
| WO | 9627336 | 9/1996 |
| WO | 2000061014 | 10/2000 |
| WO | 2003068079 | 8/2003 |
| WO | 2004045428 | 6/2004 |
| WO | 2005089202 | 9/2005 |
| WO | 2006043164 | 4/2006 |
| WO | 2009074863 | 6/2009 |

OTHER PUBLICATIONS

International Search Report and Written Opinion, PCT Application No. PCT/IB05/003151, Feb. 26, 2003.
International Search Report and Written Opinion, PCT Application No. PCT/IB08/003459, Jul. 7, 2009.
International Preliminary Report on Patentability, PCT Application No. PCT/IB05/003151, May 3, 2007.
International Preliminary Report on Patentability, PCT Application No. PCT/IB08/003459, Mar. 31, 2011.

* cited by examiner

SAFETY SCALPEL

CROSS REFERENCE TO RELATED APPLICATIONS

This application is a continuation application of U.S. application Ser. No. 11/577,768 filed Nov. 19, 2007, now abandoned, which is the U.S. national phase of International Application No. PCT/IB2005/003151, filed Oct. 21, 2005 which claims priority to U.S. Application No. 60/621,146 filed Oct. 22, 2004, the contents of each of which is incorporated herein by reference in their entireties.

FIELD OF THE INVENTION

This invention relates to surgical scalpels and, in particular, to surgical scalpels that have disposable, retractable and ejectable blades.

BACKGROUND OF THE INVENTION

Surgical scalpels have long been available. However, there is need for a scalpel with better ergonomic features while meeting rigorous occupational health and safety requirements for sharps used in medical practice. More specifically, there is need for scalpels that facilitate scalpel blade engagement and disengagement (ejection). It is desirable to minimize the need to exert pressure with fingers when mounting the blade to the blade tang and to eliminate entirely the need for direct contact with the blade to disengage it from the scalpel handle. In addition, for safe passing of scalpels among surgical personnel, it is desirable for the blade to be retracted into the handle and preferably to minimize the need for visual confirmation that the blade is retracted.

SUMMARY OF THE INVENTION

The scalpel assembly of this invention incorporates two key features enabling safe blade engagement or disengagement and safe passing among personnel during surgical procedures. For scalpel blade loading, the blade is readily positioned on the blade with one hand, and a simple retraction motion by the other hand positions the blade in a horizontal manner for entry into a guiding channel slot within the scalpel handle. During use the blade is held in the handle in a stable manner to allow for highly controlled surgical incisions without any undesirable blade mobility. For disengaging the scalpel blade, a simple extension of the blade arm, beyond the locked operational position, to a fully extended position permits the blade to disengage from its firmly fixed engagement with the blade holder, thereby enabling hands-free blade disengagement.

During use of the scalpel assembly, it may be safely passed from one person to another because the blade may be easily retracted within the handle with one hand. In addition to distinct tactile indications of positioning of the blade (in a retracted or extended position), there is a distinct auditory cue.

The scalpel assembly includes a handle and a blade arm sub-assembly for easy disassembly for cleaning, reassembly and subsequent sterilization for re-use.

DETAILED DESCRIPTION

Figure 1:
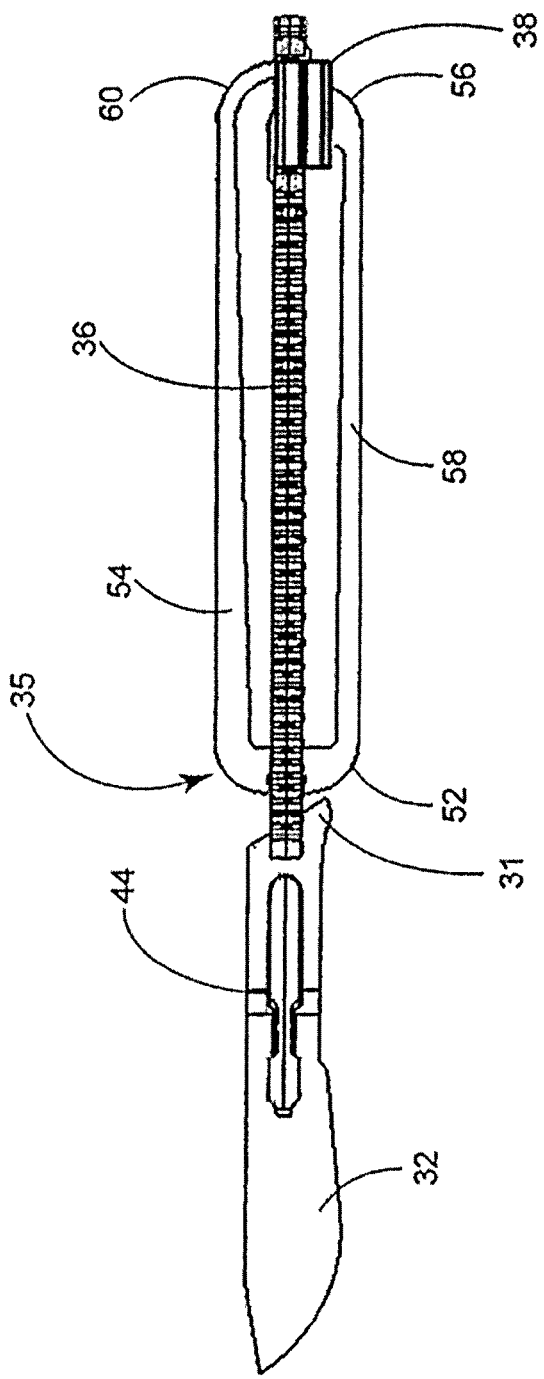
FIG. 1 is a top view of a blade arm assembly of a scalpel of this invention.
Figure 2:
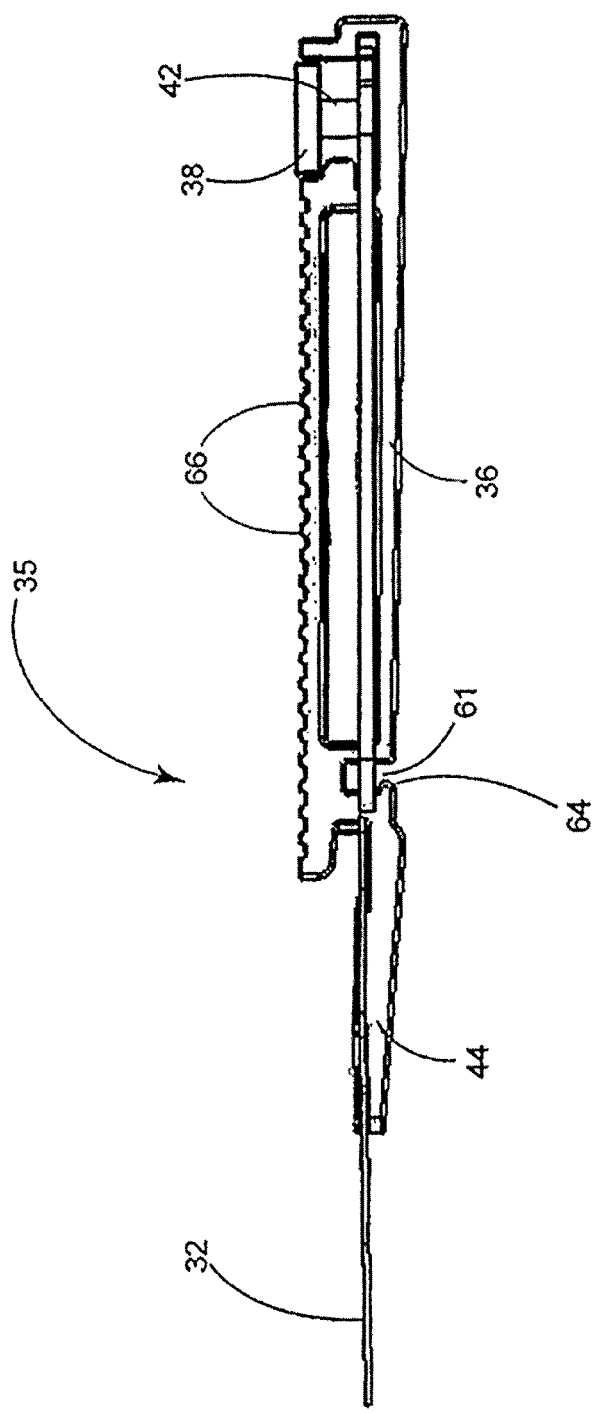
FIG. 2 is a side view of the assembly shown in FIG. 1.
Figure 3:
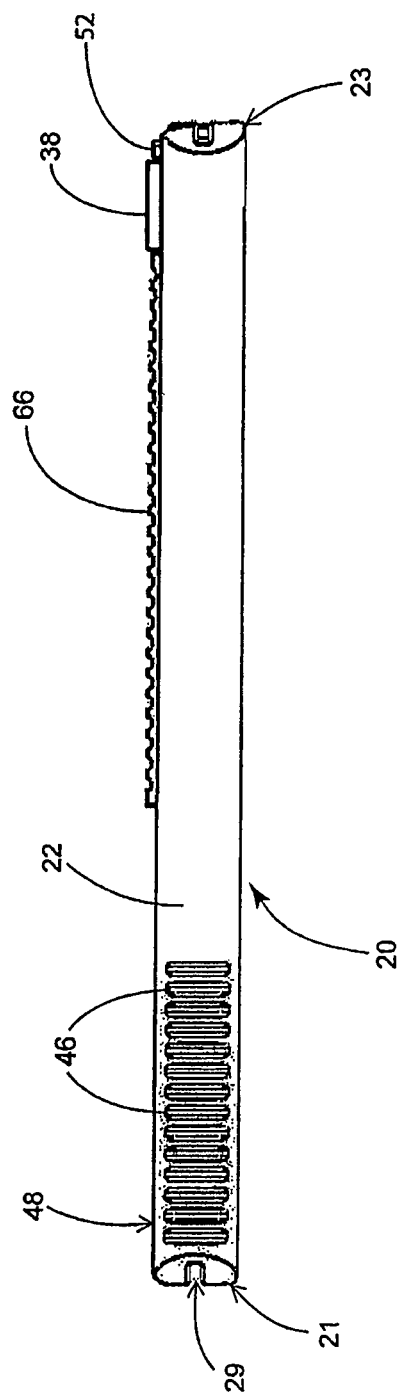
FIG. 3 is a side view of a scalpel assembly of this invention with the blade assembly retracted.
Figure 4:
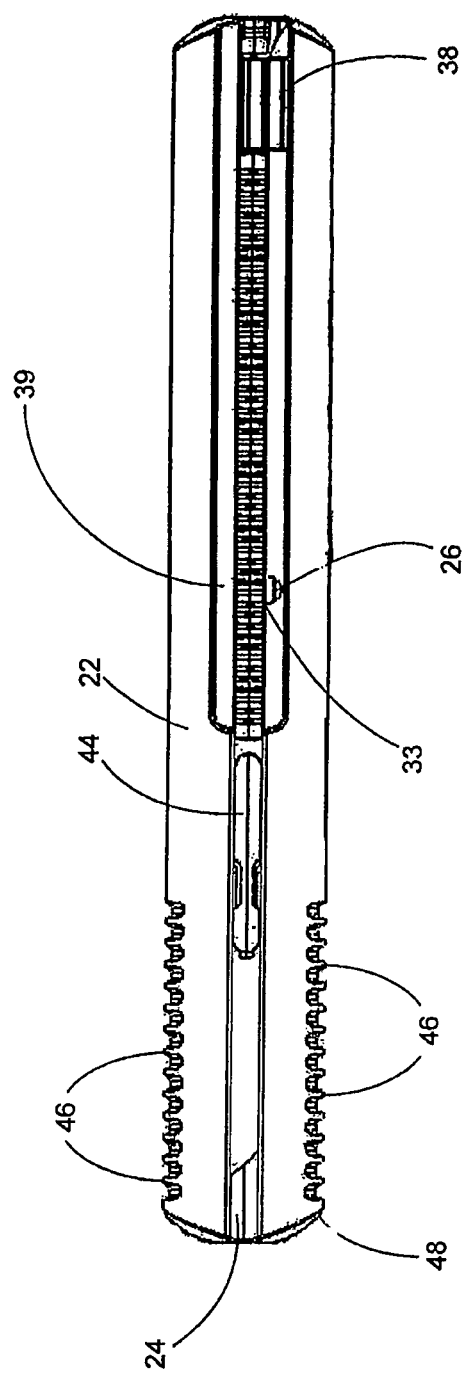
FIG. 4 is a top view of the scalpel assembly of FIG. 3, with the blade assembly retracted.
Figure 5:
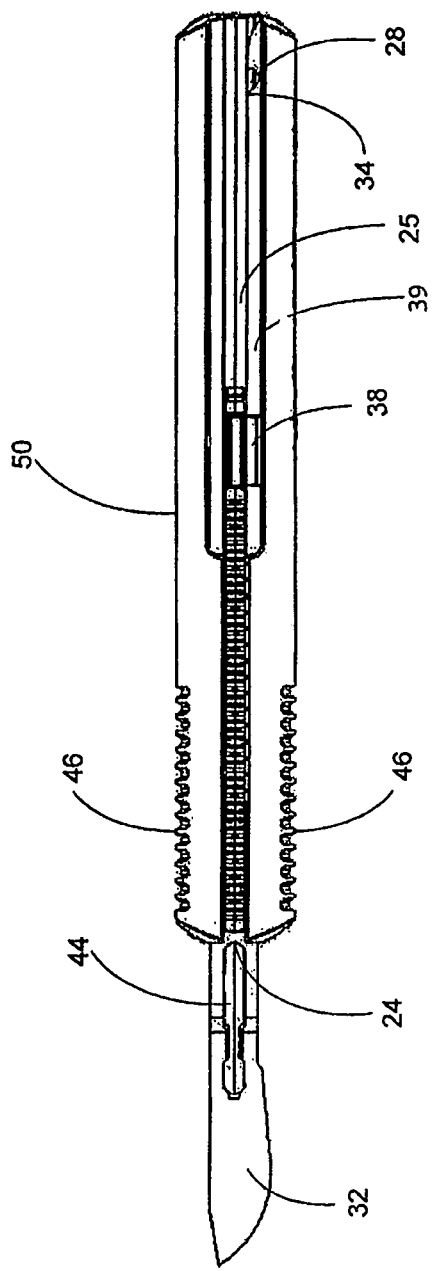
FIG. 5 is a top view of the scalpel assembly of FIG. 3, with the blade assembly extended to the position in which it is used.

A scalpel assembly of this invention includes a handle and a blade arm assembly that cooperate to provide both safe blade engagement or disengagement and safe passing during surgical procedures. The blade arm assembly, an embodiment 35 of which is shown in FIGS. 1 and 2, slides within longitudinal slots in the handle, an embodiment 20 of which is shown in FIG. 3, and may be positioned in either a blade retracted position (FIG. 4), a blade extended operational position (FIG. 5), or a fully extended blade engagement and disengagement position.

As may be seen in FIGS. 3-6, the handle 20 is an elongated body 22 preferably having a generally uniform, more or less oval cross section (best seen in FIG. 6) with a longitudinal central channel slot 24 that penetrates the handle body and two opposed internal transverse slots 29 oriented perpendicular to the central channel slot 24. All of the slots 24 and 29 extend fully from the proximal end 21 to the distal end 23 of the handle, making it relatively easy to manufacture handle 20 from a section of aluminum extrusion.

Slots 24 and transverse slots 29 together provide a T-shaped or X-shaped slot within the handle 20 within which the blade arm assembly 35 and blade 32 slide. The leading edges of slot 29 may be beveled, rounded over or otherwise eased to facilitate entry of the back end 31 of the blade into the slots 29.

A scalpel blade 32 is held on a blade holder 44 extending from one end of a blade arm 36 that slides within the central slot 24. Blade arm 36 carries a bi-cantilever element 52 (shown in FIGS. 1, 2 and 7 and further described below) that functions as a spring, and a button 38 is attached to the bi-cantilever element 52 by a pin 42. Button 38 travels within a recessed region 39, visible in FIGS. 4 and 5.

The bi-cantilever element 52 is generally flat and extends from the blade arm 36 on either side so that portions of it can be received in transverse slots 29 while the element 52 more or less surrounds a portion of blade arm 36, as may be appreciated by reference to FIGS. 1 and 2. Pin 42 projects from hole 63 (shown in FIG. 7) bi-cantilever element 52 and through central slot 24, but pin 42 is urged toward one side 25 (shown in FIGS. 5 and 6) of that slot 24 by the spring action of bi-cantilever element 52 thereby urging pin 42 to seat in one of detents 26 or 28 when it reaches those detents, thereby locking blade arm 36 in a blade extended position (with pin 42 in detent 26) or a blade retracted position (with pin 42 in detent 28). In an alternative embodiment, a face of the slot channel that opposes the detents may have a slight indentation so that the slot width is slightly wider in that region. This alternative allows additional lateral movement of the button and pin prior to movement of the blade arm, thereby providing a more distinct lateral shift of the button and pin and increasing the tactile feel of the device.

By sliding blade arm 36 so that pin 42 travels beyond detent 26 (i.e., further from detent 28), the base 31 of blade 32 will move out of transverse slot 29, thereby permitting it to lift off of tang or blade holder 44 and release from blade arm 36. With blade arm 36 in the same position, a blade 32 can easily be positioned on the blade holder 44 and then secured by sliding the blade arm 36 into the handle until pin 42 reaches at least detent 26, at which point the base 31 of blade 32 will be captured in transverse slots 29, thereby preventing it from disengaging from tang or blade holder 44.

The position of blade arm 36 in handle 20, and thus the position of blade 32 is easily manipulated with one hand by finger contact with button 38 to disengage pin 42 from the detent 26 or 28 within which it is seated and by then sliding the blade arm 36 relative to handle 20 by contact with either or both of button 38 and ridges 66. The shapes and relative positions of the components of the scalpel of this invention permit all of these manipulations to be done with one hand. Simple reversal of the scalpel blade and blade tang accommodates both left and right handed scalpel users.

As explained above, the blade arm assembly 35 consists of several components: the blade arm 36, the button 38 and pin 42, and the planar bi-cantilever element 52. The function of the bi-cantilever element 52, shown in FIG. 7, in cooperation with the button 38 and pin 42, is to control movement of the blade arm 36 within the handle 20, and to provide positively locking positions (together with audible confirmation of achievement of those positions) with the blade 32 in an extended for use or a retracted for safety position. Element 52 functions as a spring but in a planar structure that travels and functions partially within the transverse slots 29 that also serve to receive and retain blade 32 on tang or blade holder 44. Moreover, the geometry and material of element 52 is durable, capable of sterilization and otherwise highly functional in this application.

Figure 7:
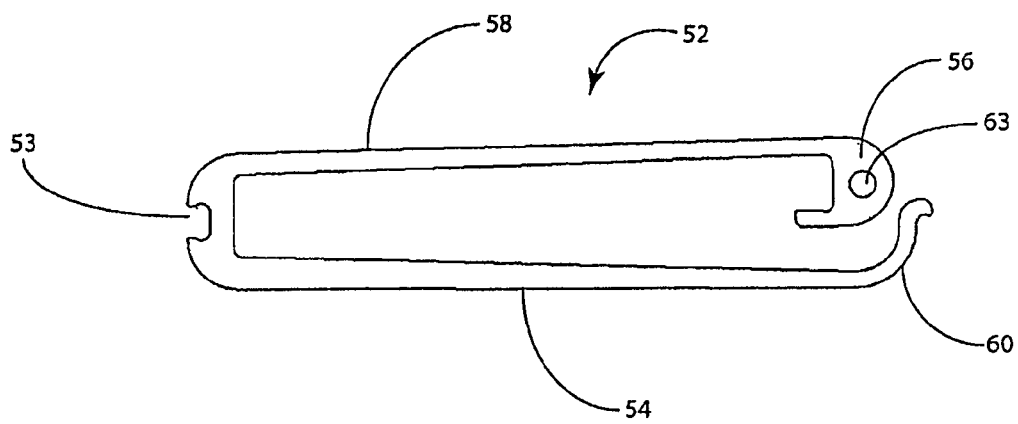
FIG. 7 is a bottom view of the bi-cantilever element of FIG. 1.

In the embodiment shown in FIG. 7, the crook 60 of one arm 54 of bi-cantilever element 52 is shaped to fit around the head 56 of the second cantilever arm 58, thereby allowing for a spring-like action limited in its inward travel by the contact between the two cantilever arms 54 and 58 as they are squeezed toward each other. The head 56 and crook 60 of the bi-cantilever element 52 align edge-to-edge in the horizontal plane (coming out of the page in FIG. 2), which restricts the lateral inward movement of the assembly 35 and provides for definitive control of the motion of button 38. In other words, the crook 60 cradles the head 56 when the element 52 is compressed. In an alternative embodiment, inward or outward motion of the button is restricted by the physical contact of the button pin with the edge of the channel slot. In this embodiment, it is not necessary for the fixed portion of the cantilever element to interact with the non-fixed section of the cantilever element to control the extent of lateral motion. As a result, the fixed cantilever portion may be shorter in length.

The assembly of button 38 and pin 42 may be permanently joined to the distal end of the bi-cantilever element 52. In another embodiment, the button 38 and pin 42 may be fastened to blade arm 36 in a manner similar to that of a semi-tubular rivet. In this manner, the scalpel assembly may be formed so that either of the arms 54 or 58 may act as the flexible member of the spring element. In yet another embodiment, both arms 54 and 58 are flexible and free to move.

The bi-cantilever element 52 may be inserted or removed from the main blade arm 36, if required, but it is normally maintained assembled to the blade arm 36. Notch 53 (shown in FIGS. 1 and 7) of bi-cantilever element 52 is adapted to receive the blade arm 36.

As shown in FIG. 2, a step-like feature 64 is located at the junction of the blade holder 44 and the rest of the blade arm 36 to allow for a ramping up motion as the blade arm 36 moves toward the distal end 23 of holder body 22, thereby positioning the scalpel blade 32 for alignment with the traverse slots 29, facilitating retraction of scalpel blade 32 into the proximal end 21 of the handle body 22. This motion of the blade arm 36 generally requires a relatively loose fit between the blade arm 36 and the bi-cantilever element 52. The ramping up motion is partially guided by a channel 61 (shown in FIG. 2) in the blade arm 36 while the bi-cantilever element 52 remains captured in the traverse slot 29. If, as an alternative to the separate blade arm 36 and element 52 assembly shown in the Figures, a one-piece molded assembly is used for arm 36 and bi-cantilever element 52, the inherent properties of the materials (such as plastics or plastic composites) could allow for a similar flexible motion to permit for horizontal blade alignment with the slots 29. Alternatively, any other suitable structure may be used to create this ramping motion. For example, the inner topmost portion of the opening of the proximal end of the handle may be slightly beveled (e.g. 30 degrees), providing a ramping force to gently push the distal end of the scalpel blade downwards and onto the blade tang.

Engagement of the button pin 42 with the detents 26 or 28 produces an audible sound, confirming the tactile sense of detent engagement with the button 38 and pin 42. The need for visual confirmation of either blade retraction or extension may be minimized by the combined tactile and auditory cues.

In the embodiment shown in the Figures, the transition area 33 (shown in FIG. 4) between the proximal detent 26 and a side of the slot includes a steeper, almost perpendicular, rise requiring an increased lateral force on the button 38 followed by a forward motion along the handle channel to allow the blade arm 36 to travel from the operational, blade extended position (with button pin 42 in detent 26) to the further extended position (in which pin 42 is located proximally to detent 26) allowing for blade disengagement. The transition area 34 (shown in FIG. 5) between the distal detent 28 and a side of the slot may be more gradual, requiring less force to travel from a retracted position to an operational position.

Uni-directional blade arm loading occurs from the distal end 23 with the detents 26 and 28 engaging the button 38 and pin 42 on the blade arm 36, automatically locking in place at either the fully retracted or extended blade positions.

The handle 22 may be easily separated from the inner components (blade arm 36, bi-cantilever element 52, pin 42 and button 38) for cleaning. During such separation, the button 38 position is maintained essentially along the axis of the channel 24 for pulling the blade arm assembly back and out from the handle body 22.

Figure 6:
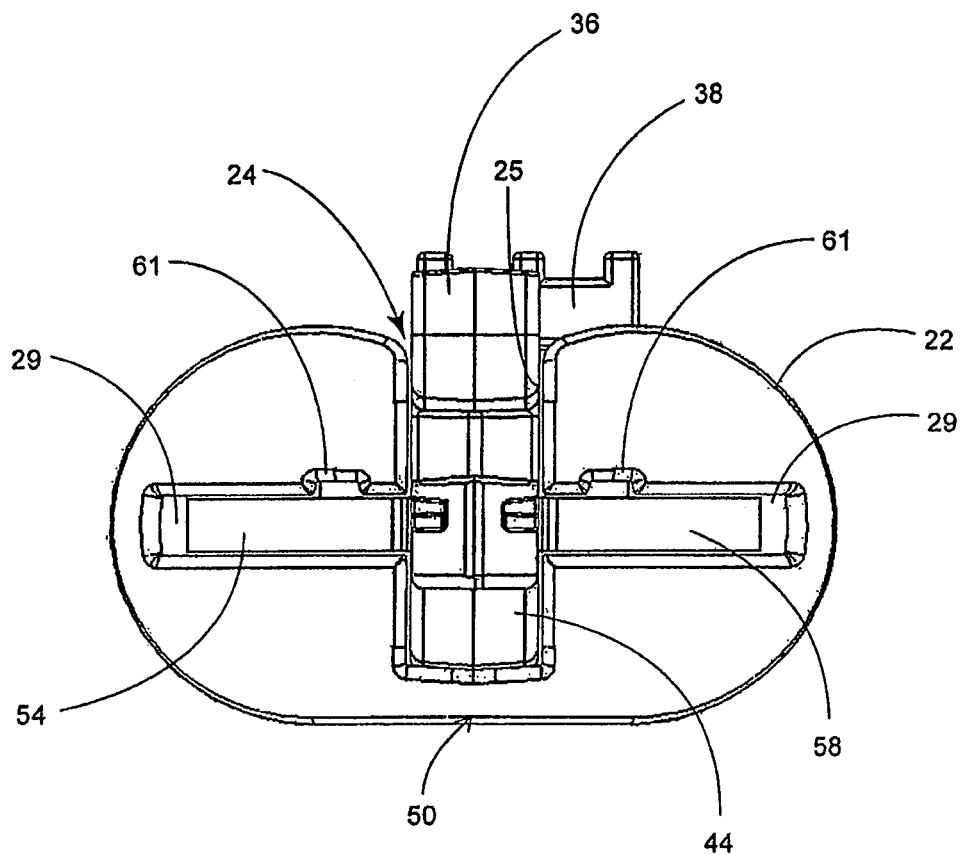
FIG. 6 is a front view of the scalpel of FIG. 3 without the blade.

The blade-securing structures of tang or blade holder 44 on the blade arm 36 are generally the same as those disclosed in U.S. patent application Ser. No. 09/937,542 filed Sep. 26, 2001, now U.S. Pat. No. 7,748,124, for Scalpel Assembly, Michael S. G. Bell, et al, inventors (PCT/1800/00426, WO 00/61014) which is incorporated herein by this reference. A scalpel handle body of this invention can accommodate in its standard configuration essentially all scalpel blades complying with ISO 7740-1985 (E) standards except for those that have a hooked or curved surface which would require a larger opening adaptation at the proximal end of the handle. As shown in FIG. 6, shallow notches 61 located on the upper inner surface of transverse slot 29 may be included in order to accommodate rib-backed scalpel blades, which are designed to prevent snapping of the blade during surgery.

For improved control and to facilitate gripping of the handle body 22, ridges 46 are positioned across the width of the handle body 22 top-most and bottom-most edges on the proximal portion 48. These ridges may be about 0.6 mm deep, or any other suitable size. Ridges 46 may cover approximately ¼-⅓ of the handle length.

Handle body 22 may include ruler markings (not shown in the Figures) imprinted or stamped on the non-slotted broad face 50 (shown in FIG. 5) of the handle body 22. In addition, the handle 22 can be made of different lengths to provide industry standard scalpel assemblies, such as #3, #3L, #4, #4L. Handle 22 may also be weighted if desired depending upon the materials used.

The top-most surface of the blade arm 36 may include ridges 66 (shown in FIG. 2) to provide adequate contact area for one-finger induced motion, either forward or backwards, of the blade arm 36.

The button 38 can be colored differently to indicate different scalpel types.

The inner assembly of blade arm 36, bi-cantilever element 52, button 38 and pin 42 can be produced as individual components and then assembled or it can be produced as a single entity by, for instance, metal injection molding or machining, or molding or otherwise fabricating of plastics or a plastic composite.

The handle body 22 and inner blade arm 36 assemblies can be produced from materials such as aluminum, stainless steel, titanium or plastic allowing for a full-range of sterilization techniques to be used (e.g. steam, gas, E-beam or gamma irradiation sterilization).

The scalpel assembly of this invention can be produced for reusable (non-disposable) or disposable systems.

As will be understood by those skilled in the art, variations in materials or manufacturing techniques and numerous other variations in the details of the protected blade scalpel handle of this invention can be made without departing from the scope and spirit of this invention as described above and in the accompanying Figures and the following claims.

The invention claimed is:

1. A scalpel handle assembly for use with a replaceable scalpel blade, the assembly comprising:
   (a) a handle comprising an elongated body, a central channel slot, a pair of opposed transverse slots, a first detent, and a second detent, and
   (b) a blade arm assembly comprising:
      (i) a button assembly comprising a button and a pin, and
      (ii) a blade arm comprising a blade tang positionable relative to the handle alternatively:
         (1) with the pin of the button assembly received in the first detent wherein the blade is withdrawn entirely into the handle,
         (2) with the pin of the button assembly received in the second detent wherein the blade projects from the handle with the base of the blade captured in the pair of opposed transverse slots thereby retaining the blade on the tang, wherein the blade is locked in position and operational, or
         (3) with the pin of the button assembly extended beyond the second detent wherein the blade is entirely outside the handle with the base of the blade extended beyond the pair of opposed transverse slots wherein the blade is not secured to the blade arm, and wherein the blade is removable without contacting the blade,
   (c) wherein a first transition between the first detent and a side of the central channel slot is more gradual than a second transition between the second detent and the side of the central channel slot requiring an increased lateral force to disengage from a blade projecting position to a fully projected position for removing the blade from the blade tang,
   (d) wherein depression of the button permits advancement and retraction of the blade arm assembly.

2. A scalpel handle assembly for use with a replaceable scalpel blade, the assembly comprising:
   (a) a handle comprising an elongated body penetrated by a first longitudinal slot open to the outside of the handle, and a pair of opposed transverse slots perpendicular to the first slot, and
   (b) a blade carrier assembly comprising:
      (i) a blade arm comprising a blade tang attached to an arm body positionable within the first slot, and
      (ii) a spring associated with the blade arm to secure the blade arm in a selected one of two positions with a blade projecting from the handle for use or retracted into the handle for safety;
   (c) wherein a pin is received in a first detent when the blade is projecting from the handle for use;
   (d) wherein the pin is received in a second detent when the blade is retracted into the handle for safety;
   (e) wherein a first transition between the second detent and a side of the first slot is more gradual than a second transition between the first detent and the side of the first slot requiring an increased lateral force to disengage from a blade projecting position to a fully projected position for removing the blade from the blade tang.

3. The scalpel handle assembly of claim 2, wherein a button or knob facilitates manipulation of the pin.

4. The scalpel handle assembly of claim 2, wherein the pin is secured to the spring and is received in one of the two detents in the handle.

5. A surgical scalpel comprising:
   (a) a blade arm assembly that slides within a handle, wherein the blade arm assembly comprises a blade arm, a button assembly and a spring, the spring comprising a bi-cantilever element,
   (b) the handle comprising a pair of transverse slots that receive the blade arm assembly, wherein a blade is secured to the blade arm assembly by a portion of the blade attached to the blade arm assembly being captured in the pair of transverse slots,
   (c) wherein the blade is secured to the blade arm assembly in one of two positions:
      (i) a fully retracted position with the entire blade withdrawn into the handle, or
      (ii) a protruding operational position with a base of the blade captured in the pair of transverse slots with a cutting edge of the blade projecting from the handle for use, and
   (d) wherein the blade is positionable in a fully extended position for engaging and disengaging the blade with the base of the blade extending beyond the pair of transverse slots such that the blade is removable from the blade arm assembly without contacting the blade and
   (e) wherein a free end of a first cantilever section of the bi-cantilever element is shaped to fit around a curved end of a second cantilever section of the bi-cantilever element, thereby allowing for a spring-like action limited in its inward travel by the contact of the two cantilever sections as they are squeezed toward each other.

* * * * *